United States Patent [19]

Packard

[11] 4,440,258
[45] Apr. 3, 1984

[54] TUNABLE STETHOSCOPE

[75] Inventor: Thomas J. Packard, Somerset, Wis.

[73] Assignee: Minnesota Mining & Manufacturing Company, St. Paul, Minn.

[21] Appl. No.: 377,395

[22] Filed: May 12, 1982

[51] Int. Cl.³ .......................... A61B 7/02; H04R 25/00
[52] U.S. Cl. .................................................. 181/137
[58] Field of Search .............. 181/131, 132, 137, 157, 181/158, 172; 179/1 ST

[56] References Cited

U.S. PATENT DOCUMENTS

| | | | |
|---|---|---|---|
| 1,485,124 | 2/1924 | Myres | 181/137 |
| 3,067,833 | 12/1962 | Bodenger | 181/137 |
| 3,108,652 | 10/1963 | Littmann | 181/131 |
| 3,109,508 | 11/1963 | Cefaly | 181/137 |
| 3,152,659 | 10/1964 | Littmann | 181/137 |
| 3,157,246 | 11/1964 | Howell | 181/137 |
| 3,179,204 | 4/1965 | Cefaly | 181/137 |
| 3,215,224 | 11/1965 | Machlup | 181/137 |
| 3,224,526 | 12/1965 | Weber | 181/137 |
| 3,276,536 | 10/1966 | Littmann | 181/137 |
| 3,303,903 | 2/1967 | Speelman | 181/131 |
| 3,307,650 | 3/1967 | Howell | 181/137 |
| 3,472,336 | 10/1969 | Dahl | 181/131 |
| 3,515,239 | 6/1970 | Machlup et al. | 181/137 |
| 3,951,230 | 4/1976 | Littmann | 181/131 |
| 4,270,627 | 6/1981 | Hill | 181/131 |

FOREIGN PATENT DOCUMENTS 69226 12/1976 U.S.S.R. .

OTHER PUBLICATIONS

A. B. Cohen, Hi-Fi Loudspeakers and Enclosures, Hayden Book Company, N.J., pp. 24–25, 56–58 and 83–85, (1968).

Primary Examiner—Benjamin R. Fuller
Attorney, Agent, or Firm—Donald M. Sell; James A. Smith; Robert W. Sprague

[57] ABSTRACT

A stethoscope head comprising a body member having a first generally bell-shaped recess, a diaphragm, a suspension member for connecting the diaphragm to the body member, and an immobilizing means located within the first recess. The suspension member affords movement of the diaphragm in a direction generally perpendicular to the plane of the diaphragm without the shape of or lateral tension in the diaphragm changing substantially. The suspension member also permits at least one of the diaphragm and the suspension member to contact the immobilizing means to cause the acoustical stiffness of the diaphragm to increase significantly. In a preferred embodiment the suspension member comprises a compliant ring and the immobilizing means comprises an O-ring situated circumjacent a plate-like member having a centrally sloping depression in its surface.

11 Claims, 9 Drawing Figures

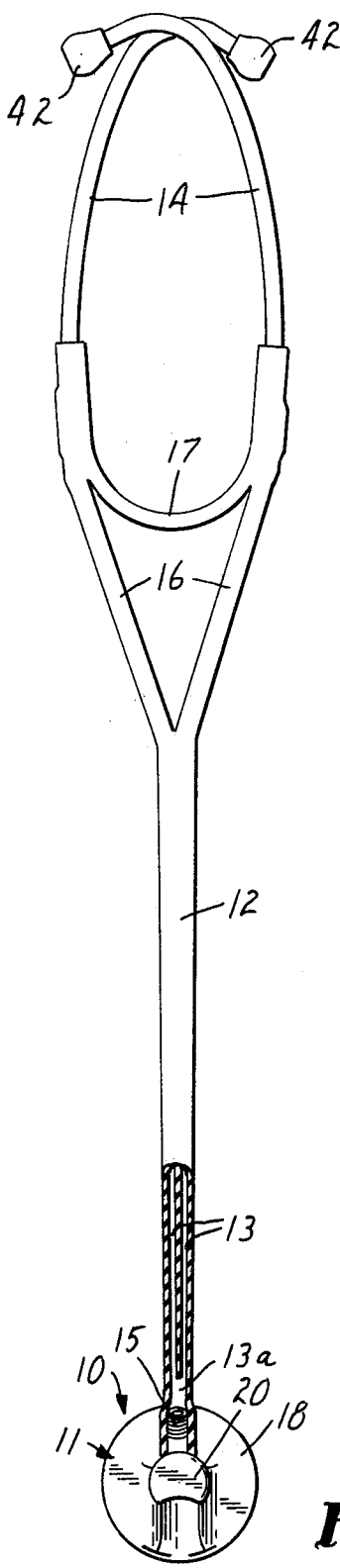
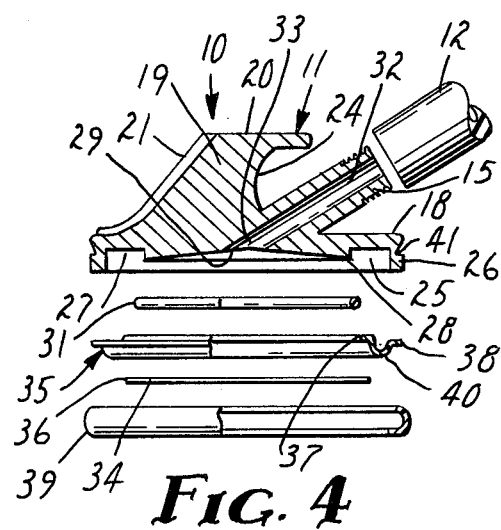
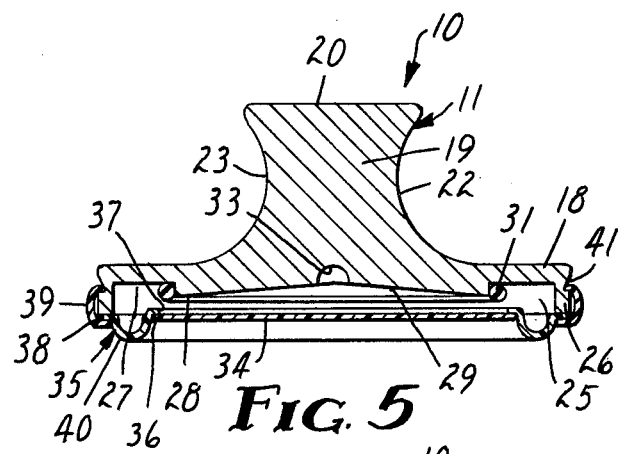
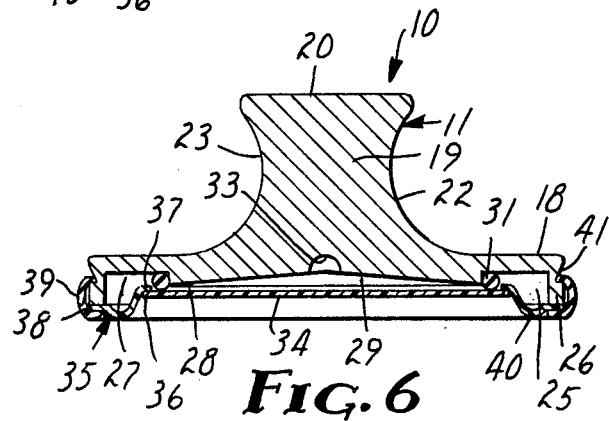
Fig. 1
Fig. 4
Fig. 5
Fig. 6

TUNABLE STETHOSCOPE

The present invention relates to stethoscopes. More particularly, it relates to stethoscopes which can be adjusted or tuned to vary the frequency response of the stethoscope head.

Complete diagnosis of a patient often requires that a physician monitor both low frequency and high frequency sounds associated with, for example, the heart. In respect to the heart, it is important that the physician alternate rapidly between the monitoring of low frequency and high frequency sounds so that the physician does not lose the impression from the previously heard heartbeat before the next beat is heard. If the process of alternating between monitoring low frequency and high frequency sounds requires considerable time, a significant number of heartbeats may unfortunately go undetected.

Stethoscope head constructions are known which comprise diametrically opposed diaphragm and open bells which are adapted for detecting low frequency sounds and high frequency sounds, respectively. So-called "dual head" stethoscopes of this type are described, for example, in U.S. Pat. Nos. 3,108,652 (Littman), 3,152,659 (Littman), 3,215,224 (Machlup), 3,224,526 (Weber), 3,276,536 (Littman), 3,303,903 (Speelman), and 3,515,239 (Machlup et al). The diaphragm used in such dual head stethoscopes has a relatively high degree of acoustical stiffness which provides sensitivity to high frequency sounds. The open bell portion of the dual-head stethoscope is adapted to pick up low frequency sounds. To alternate between the monitoring of low frequency and high frequency sounds, the chestpiece must be removed from the patient's skin, rotated between the open-bell and diaphragm sides and replaced on the skin. Unfortunately, this process may require considerable time and may result in a significant number of heartbeats going undetected.

Stethoscope head constructions are known which are designed to permit detection of a range of frequencies without the physician having to remove the stethoscope head from the patient's skin. For example, U.S. Pat. No. 3,109,508 (Cefaly) discloses a stethoscope head which comprises three sound-receiving heads. One of the sound-receiving heads comprises a diaphragm which can be distorted to vary the volume of the chamber enclosed by the diaphragm. Concomitant with the change in volume of the chamber is a change in the acoustical stiffness of the diaphragm. The ability to change the volume of the chamber is said to permit "tuning in" of the particular sound or vibration to be detected. Unfortunately, the frequency response of this particular sound receiving head is not believed to be optimized. Specifically, even in its totally relaxed state (i.e., the position in which the acoustical stiffness is minimized and the sensitivity to low frequency sounds is maximized), the diaphragm still exhibits an acoustical stiffness which is not optimized for detection of low frequency sounds. Consequently, it is often necessary to employ one of the other two sound receiving heads in the detection of sounds of such frequencies.

U.S. Pat. No. 3,157,246 (Howell) discloses a stethoscope head construction comprising a diaphragm which is upwardly arched from the bowl of the stethoscope head. The acoustical stiffness of the diaphragm is varied by varying the pressure with which it is applied to the body. In this manner, the frequency response of the stethoscope is said to be widened. It is believed, however, that, as with the stethoscope head described in Cefaly, the minimum acoustical stiffness of the diaphragm of this stethoscope head is not low enough to optimize sensitivity to low frequency sounds. Furthermore, the sensitivity to high frequency sounds is also somewhat compromised by this design construction.

Although numerous attempts have been made to provide a practical stethoscope head which permits auscultation of both low and high frequency sounds through one surface, prior to the present invention, none have been successful in providing a high level of low frequency sounds and a clear differentiation between low and high frequency sounds.

The present invention overcomes the problems of the prior art and successfully fulfills the aforementioned needs. According to the present invention there is provided a stethoscope head comprising:

- a body member having a first generally bell-shaped recess with an innermost central portion, an outer rim portion, and a bore extending through the body member communicating with the central portion of the recess;
- a diaphragm having a peripheral edge portion and a predetermined surface contour overlying at least a portion of the first recess and moveably connected to the outer rim portion of the recess;
- a suspension member located between the outer rim portion of the recess and the peripheral edge portion of the diaphragm for moveably connecting the peripheral edge portion of the diaphragm to the outer rim portion of the recess to provide a first acoustical stiffness for the diaphragm, and for affording movement of the diaphragm in a direction generally perpendicular to the plane of the diaphragm between a normal outer position to which the diaphragm is biased by the suspension member and an inner position more closely adjacent the central portion of the recess without substantially changing the surface contour of or lateral tension in the diaphragm during the movement; and
- immobilizing means situated on the body member located within the first recess at about the boundary between the outer rim and the central portion, the immobilizing means adapted to be contacted by at least one of the diaphragm and the suspension member and to substantially immobilize the diaphragm when the diaphragm is in the inner position so that the stethoscope head will pass low frequency sounds and attenuate high frequency sounds when the diaphragm is in the outer position and between the outer and inner positions, and when the diaphragm is in the inner position the acoustical stiffness of the diaphragm will be significantly higher than the first acoustical stiffness so that the head will pass high frequency sounds and attenuate low frequency sounds.

The present invention also provides a preferred stethoscope head comprising:

- a body member having a first generally bell-shaped recess with an innermost central portion, an outer rim portion, and a bore extending through the body member communicating with the central portion of the first recess;
- a diaphragm having a peripheral edge portion and a predetermined surface contour overlying at least a portion of the first recess and moveably connected to the outer rim portion of the recess;

a compliant ring having an inner edge, an outer edge and a central curved portion, the inner edge being attached to the peripheral edge portion of the diaphragm and the outer edge being attached to the outer rim portion of the first recess to provide a first acoustical stiffness for the diaphragm, the complaint ring permitting movement of the diaphragm in a direction generally perpendicular to the plane of the diaphragm between a normal outer position to which the diaphragm is biased by the compliant ring and an inner position more closely adjacent the central portion of the first recess without substantially changing the surface contour of or the lateral tension in the diaphragm during the movement; and immobilizing means situated on the body member and located within the first recess at about the boundary between the outer rim portion and the inner central portion and together with the inner central portion forming a second shallow and generally conical-shaped recess within the first recess, the immobilizing means adapted to be contacted by the diaphragm and to immobilize the diaphragm when the diaphragm is in the inner position so that the stethoscope head will pass low frequency sounds and attenuate high frequency sounds when the diaphragm is in the outer position and between the outer and inner positions, and when the diaphragm is in the inner position the acoustical stiffness of the diaphragm will be significantly higher than the first acoustical stiffness so that the stethoscope head will pass high frequency sounds and attenuate low frequency sounds.

The stethoscope head of the present invention permits detection of both low frequency and high frequency sounds through one surface, and, accordingly, does not require removal from the patient when it is desired to alternate between the monitoring of low frequency and high frequency sound. This construction permits the physician to alternate rapidly between the monitoring of low frequency and high frequency sounds, thereby assuring that no significant number of heartbeats will go undetected. Low frequency sounds (i.e., sounds of less than or equal to about 200 Hz) are monitored by placing the diaphragm of the stethoscope head on the patient in light contact with the patient's skin or clothing. In this mode of operation, the suspension member permits the diaphragm to float freely in a spaced location from the immobilizing means such that the diaphragm exhibits a low acoustical stiffness. Also, the diaphragm encloses a relatively large volume of the first bell-shaped recess. Due to the low acoustical stiffness exhibited by the diaphragm and the relatively large volume that the diaphragm encloses, the diaphragm is suitably sensitive to a wide range of low frequency sounds. High frequency sounds (i.e. sounds of greater than about 200 Hz) are detected by exerting sufficient pressure on the stethoscope head to cause at least one of the diaphragm and the suspension member to contact the immobilizing means such that the accoustical stiffness of the diaphragm increases significantly. Additionally, the diaphragm now encloses a relatively small volume of the first bell-shaped recess. Due to the greater acoustical stiffness exhibited by the diaphragm and the relatively smaller volume enclosed by the diaphragm, the diaphragm is suitably sensitive to a wide range of high frequency sounds.

The stethoscope head of the present invention also desirably includes a bell-shaped recess which is larger than would be practical where the recess was not enclosed by a diaphragm. A larger bell-shaped recess is desirable since sensitivity to sounds increases with increases in the surface area of the skin which is encompassed by the periphery defining the recess. In the absence of a diaphragm, there is greater potential for the skin of a patient to occlude the large recess, thereby affecting adversely the sensitivity of the stethoscope head.

DESCRIPTION OF THE DRAWINGS

The present invention will be more easily understood by reference to the following drawings in which:

FIG. 1 is an elevational view of a stethoscope comprising an embodiment of a stethoscope head in accordance with the present invention, parts thereof broken away and shown in section;

FIG. 4 is an exploded sectional view similiar to that in FIG. 3;

FIG. 5 is a cross sectional view taken along the line 5—5 of FIG. 2;

FIG. 6 is a cross sectional view similiar to that of FIG. 5 but illustrating the embodiment in a different mode;

Figure 2:
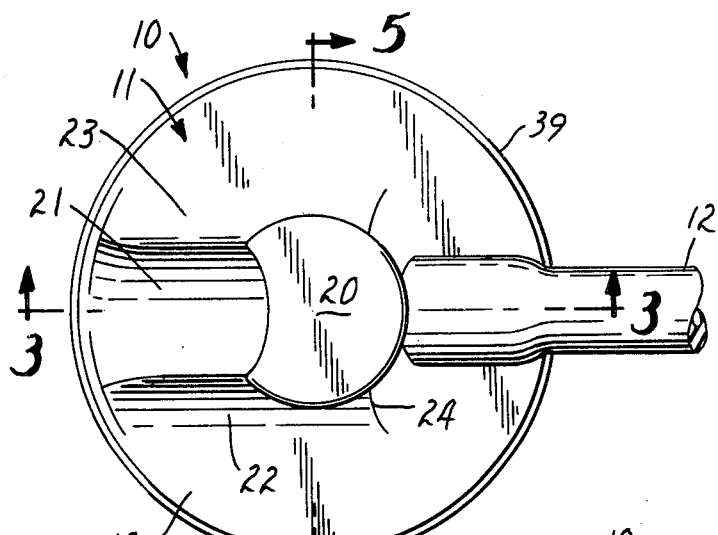
FIG. 2 is an enlarged plan view of the embodiment of the stethoscope head illustrated in FIG. 1.

As used in the instant specification and claims, "acoustical stiffness" of the diaphragm designates the mechanical stiffness of the diaphragm as influenced by the mechanical stiffness of the diaphragm material itself, the thickness of the diaphragm, the shape of the diaphragm, the diameter of the diaphragm, and the manner in which the diaphragm is attached to the stethoscope head. The phrase "plane of the diaphragm" refers to the generally planar surface of the diaphragm.

FIGS. 1-6 illustrate a preferred embodiment of a stethoscope head of the present invention. Referring first to FIG. 1, stethoscope head 10 comprises body member 11 formed of conventional material utilized in the fabrication of stethoscope heads, viz., metals such as stainless steel and aluminum, plastic, and wood. Stethoscope head 10 is attached to a conventional headset such as that described in U.S. Pat. No. 4,200,169 which comprises elongated flexible tubing 12 which contains dual air passages 13 which run side-by-side for a major portion of the distance between stethoscope head 10 and ear tubes 14. In the lower end of flexible tubing 12 which attaches to stethoscope head 10, passages 13 merge into a single passage 13a adapted to be coupled to stem fitting 15 of stethoscope head 10. The upper end of flexible tubing 12 bifurcates into coupling arms 16, each of which attaches to one of the ear tubes 14 and each of which contains one of the ear tips 42. Ear tubes 14 are secured together by tubing 17 which encloses a conventional prestressed leaf spring (not illustrated) as described in U.S. Pat. No. 4,200,167.

Referring to FIGS. 1–6, it is seen that body member 11 comprises a substantially disk-like portion 18 and column 19 emanating therefrom. Top 20 of column 19 is substantially flat. Front section 21 of column 19 is sloped away from top 20, is concave in configuration and is curved to meet the top surface of disk-like portion 18. Side sections 22 and 23 and back section 24 are arcuate in configuration. The shape of body member 11 permits the physician to grasp it in one of two particularly convenient ways. The physician may grasp column 19 from the top with the index finger being placed on front section 21 and each of the thumb and the middle finger being placed on opposite sides of column 19 adjacent top 20. Alternatively, the physician may place the index finger and middle finger adjacent disk 18 on opposite sides of column 19 (with fitting 15 passing between those fingers).

Referring now to FIGS. 3, 4, 5, and 6, it is seen that body member 11 has a first generally bell-shaped recess 25, recess 25 being defined by side wall 26, outer rim portion 27, and inner central portion or plate-like member 28. Second conical-shaped recess 29 is defined by inner central portion or plate-like member 28 which is integral with body member 11 and has a centrally sloping depression in its surface and O-ring 31 which is situated circumjacent plate-like member 28 and retained thereon. O-ring 31 is located at about the boundary between the outer rim portion 27 and inner central portion or plate-like member 28. O-ring 31 has a thickness which is slightly greater in dimension than the maximum thickness of inner central portion or plate-like member 28 at its periphery and is preferably formed of an elastomeric material such as neoprene. It is O-ring 31 which is the immobilizing means in this embodiment. Body member 11 also comprises bore 32 extending from fitting 15 through body member 11 to aperture 33 within bell-shaped first recess 25 and conical-shaped second recess 29.

Diaphragm 34 overlays the entirety of second conical-shaped recess 29 (and inner central portion or plate-like member 28) and at least a portion of first bell-shaped recess 25 to permit contact of diaphragm 34 with O-ring 31. Diaphragm 34 may comprise any material which is known in the art as being suitable for use as a diaphragm. Examples of suitable materials include plastics such as polyester, fiberglass-reinforced plastics, and polystyrene and metals such as stainless steel. A suitable thickness for diaphragm 34 is about 5 to 20 mils (0.013 to 0.051 centimeters). The preferred thickness for diaphragm 34 is about 10 to 12 mils (0.025 to 0.030 centimeters). A preferred diaphragm comprises a 10 mil-thick (0.025 centimeter-thick) epoxy resin-fiberglas laminate.

Surrounding diaphragm 34 is suspension member or compliant ring 35 which suspends diaphragm 34 across the first bell-shaped recess 25 and allows diaphragm 34 to move in a direction generally perpendicular to the plane of the diaphragm. Compliant ring 35 is generally horseshoe-shaped in cross-section having an inner edge 37 and an outer edge 38 on either side of curved portion 40. Compliant ring 35 is attached to peripheral edge portion 36 of diaphragm 34 at inner edge 37. Outer edge 38 is attached to first bell-shaped recess 25 by means of a retaining ring or plastic fitting 39 which engages notch 41 of body member 11.

Compliant ring 35 comprises a resilient material and curved portion 40 readily deforms to provide facile movement of the diaphragm 34. This construction of compliant ring 35 provides a first acoustical stiffness for diaphragm 34 and permits movement of diaphragm 34 in a direction generally perpendicular to the plane of diaphragm 4 between a normal outer position to which diaphragm 34 is biased by compliant ring 35 and an inner position more closely adjacent central portion 28. When diaphragm 34 is in the inner position it is in contact with O-ring 31 and exhibits a significantly higher acoustical stiffness than the first acoustical stiffness. The surface contour of and the lateral tension in diaphragm 34 do not change substantially during movement of diaphragm 34 between the outer position and the inner position.

Examples of suitable materials for compliant ring 35 are elastomeric polyurethanes, silicone rubbers, thermoplastic rubbers, neoprenes and latexes. A suitable thickness for compliant ring 35 is about 6 to 15 mils (0.015 to 0.038 centimeters). The preferred thickness for compliant ring 35 is 8 to 10 mil. A preferred ring 35 comprises an ether-based polyurethane film (e.g., those films which are commercially available under the trade designations "MP 1880" and "MP 2080" from J. P. Stevens Co.). The radius of curvature of convolution 40 is preferably 0.031 to 0.062 inches (0.079 to 0.16 centimeters). It is to be understood that compliant ring 35 and diaphragm 34 may be formed as an integral member during fabrication.

Compliant ring 35 is generally air-impervious. As a result, it may be desirable to provide diaphragm 34 with a hole 30 (see FIG. 3) therein in order to facilitate movement of the diaphragm from its position adjacent second conical-shaped recess 29 when it is desired to monitor high frequency sounds. In the absence of such a hole, an air-tight system is created within stethoscope head 10 when the stethoscope is in use (i.e., when it is connected to ear tubes which have been inserted into a physician's ears). Such an air-tight system may result in a formation of a vacuum which can inhibit facile movement of diaphragm 34 from its position adjacent second conical-shaped recess 29.

The response of stethoscope head 10 to low frequency and high frequency sounds is affected by several parameters. The thickness of diaphragm 34 affects the response and suitable thicknesses for diaphragm 34 have been discussed hereinabove. Also, the relative dimensions of first bell-shaped recess 25 and second conical-shaped recess 29 affect the response. The following have been found to be suitable dimensions for first bell-shaped recess 25 and second conical-shaped recess 29. First bell-shaped recess 25 has a diameter (as defined by sidewall 26) of 2 inches (5.10 centimeters) and has a volume (as defined by diaphragm 34 and compliant ring 35 when no pressure is exerted on the exterior surface of diaphragm 34) of approximately 0.325 in$^3$ (5.33 cm$^3$). Second conical-shaped recess 29 has a diameter (as defined by O-ring 31) of 1.5 inches (3.8 centimeters) and a volume (as defined by diaphragm 34 when it is in contact with O-ring 31) of approximately 0.059 in$^3$ (0.97 cm$^3$). The distance that diaphragm 34 travels from its equilibrium position to its position in which it is in contact with O-ring 31 is approximately 0.070 inches (0.18 centimeters). As indicated above, diaphragm 34 is of a diameter which is greater than the diameter of second conical-shaped recess 29 in this embodiment. A diaphragm having a 1.75 inch (4.45-centimeter) diameter has been found to be suitable in a stethoscope head comprising first bell-shaped recess 25 and second conical-shaped recess 29 of the above indicated dimensions. A compliant ring 35 which includes curved portion 40 having a radius of curvature of 0.047 inches (0.12 centimeters) has been found to provide the desired freedom of movement of diaphragm 34.

Figure 7:
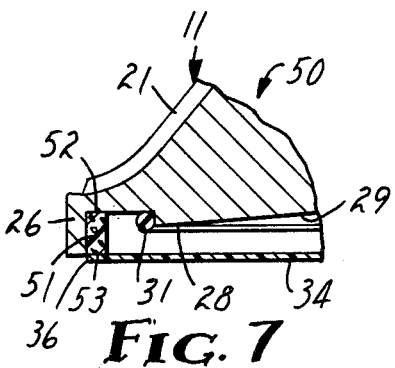
FIG. 7 is a partial cross-section of an alternative embodiment of a stethoscope head in accordance with the present invention.

FIG. 7 illustrates an alternative embodiment of a stethoscope head of the present invention in which the suspension member is a foam ring. Stethoscope head 50 comprises body member 11 (illustrated also in FIGS. 1-6 and described above) which has been modified such that the exterior surface of sidewall 26 is flat; a plastic fitting is not needed in this embodiment to connect the suspension member and diaphragm to body member 11. O-ring 31 is situated circumajacent plate-like member 30 and retained thereon as described above in connection with FIGS. 1-6. Foam ring 51 is situated adjacent the interior surface of side wall 26. Top surface 52 of foam member 51 is attached to bottom wall 27 and peripheral edge 36 of diaphragm 34 is attached to bottom surface 53 of foam member 51, attachment in each case being provided, for example, by adhesive means. Foam member 51 should be of a dimension which permits it to retain diaphragm 34 in a suitable normal outer position when foam member 51 is in its relaxed state. Foam member 51 comprises a resilient material and may be either open-cell or closed-cell in structure.

Figure 8:
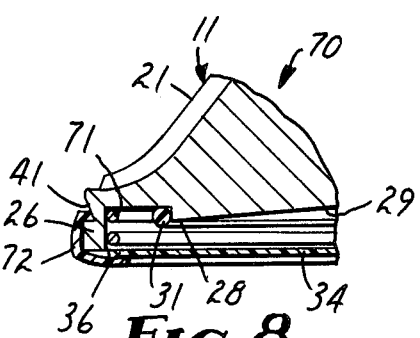
FIG. 8 is a partial cross-section of yet another embodiment of a stethoscope head in accordance with the present invention.

FIG. 8 illustrates yet another embodiment of a stethoscope head of the present invention in which the suspension member is a conventional compression spring 71. Stethoscope head 70 comprises body member 11 (illustrated also in FIGS. 1-6 and described above). O-ring 31 is situated circumjacent plate-like member 30 and retained thereon as described above in connection with FIGS. 1-6. The diameter of compression spring 71 is less than the diameter of diaphragm 34 such that peripheral edge 36 of diaphragm 34 is in contact therewith. Plastic fitting 72 overlaps peripheral edge 36 of diaphragm 34 and functions to retain the diaphragm 34 and compression spring 71 composite within first bell-shaped recess 25. Plastic fitting 72 engages notch 41 of body member 11.

Other immobilizing means which are suitable for employment in the stethoscope heads of the present invention include machined ridges, molded ridges, and inserts (e.g., plastic inserts).

It is contemplated that the acoustical stiffness of the diaphragm can be increased suitably by contact of the suspension member with the immobilizing means. For example, where the suspension member comprises a compliant ring similar to compliant ring 35 above, the desired increase in acoustical stiffness in the diaphragm can be achieved by contact of the suspension member and not the diaphragm with the immobilizing means. The portion of the suspension member which contacts the immobilizing means should be situated such that the diaphragm is substantially immobilized upon such contact.

Figures 3, 9:
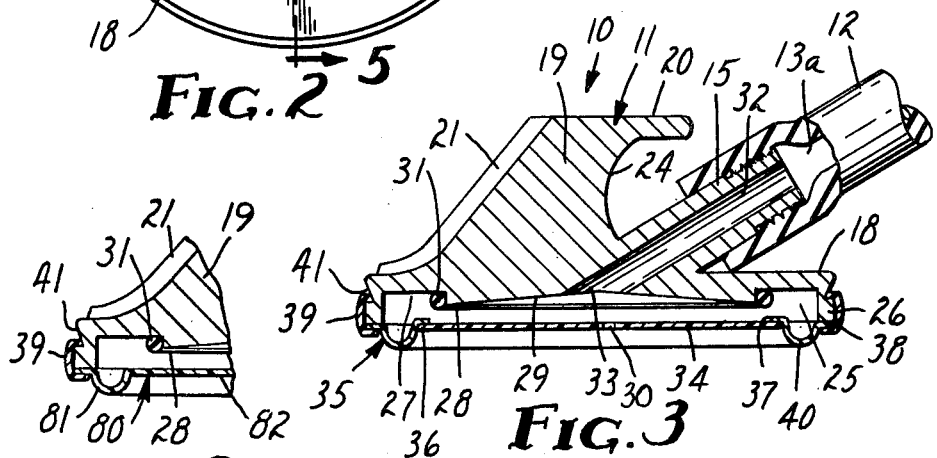
FIG. 3 is a cross sectional view taken along the line 3—3 of FIG. 2.
FIG. 9 is a partial cross-section of an alternative embodiment in accordance with the present invention.

It is also believed that the diaphragm and suspension member may be formed from a single sheet or film of material. FIG. 9 illustrates an integral member 80 into which diaphragm 82 and suspension member 81 are formed. In this regard it is to be understood that the term "diaphragm" as used in the instant application and claims designates that portion of the diaphragm-suspension member composite which substantially overlies the inner central portion 28 of the body member and is capable of undergoing the desired planar movement without a substantial change in surface contour or lateral tension.

Discussing the operation of stethoscope heads of the present invention, reference is made again to the preferred embodiment and to FIGS. 5 and 6 in particular. FIG. 5 illustrates stethoscope head 10 in a mode of operation in which low frequency sounds are passed and high frequency sounds are attenuated. Diaphragm 34 is maintained by compliant ring 35 in a spaced location from O-ring 31. Due to the resiliency of compliant ring 35 and the presence of curved portion 40 therein, diaphragm 34 is able to float relatively freely within larger, first bell-shaped recess 25 and, as a result, exhibits an acoustical stiffness which is suitably sensitive to low frequency sounds. This mode of operation is achieved by contacting the stethoscope head 10 with the patient's skin in such a manner that essentially no pressure (i.e. only a light pressure which is not sufficient to cause diaphragm 34 to contact O-ring 31 is exerted on the exterior surface of diaphragm 34.

FIG. 6 illustrates stethoscope head 10 in a mode of operation in which high frequency sounds are passed and low frequency sounds are attenuated. Compliant ring 35 has deformed allowing diaphragm 34 to contact the O-ring 31 in such a manner that an essentially airtight seal between diaphragm 34 and O-ring 31. If sufficient pressure is exerted on the exterior surface of diaphragm 34, diaphragm 34 will be in rigid contact with O-ring 31 and will exhibit a significantly increased acoustical stiffness over that exhibited by diaphragm 34 when diaphragm 34 is spaced from O-ring 31. This mode of operation is achieved by contacting stethoscope head 10 with the patient's skin in such a manner that an effective amount of pressure is exerted on diaphragm 34 to cause it to contact O-ring 31 completely and rigidly.

It is to be understood that other variations and modifications can be made without departing from the spirit and scope of the invention.

What is claimed is:

1. A stethoscope head comprising:
   a body member having a first generally bell-shaped recess with an innermost central portion, an outer rim portion and a bore extending through said body member communicating with said central portion of said first recess;
   a diaphragm having a peripheral edge portion and a predetermined surface contour overlying at least a portion of said first recess and moveably connected to said outer rim portion of said recess;
   a suspension member located between said outer rim portion of said first recess and the peripheral edge portion of said diaphragm for connecting said peripheral edge portion of said diaphragm to said outer rim portion of said recess to provide a first acoustical stiffness for said diaphragm, and for affording movement of said diaphragm in a direction generally perpendicular to the plane of said diaphragm between a normal outer position to which said diaphragm is biased by said suspension member and an inner position more closely adjacent said central portion of said first recess without substantially changing the surface contour of or lateral tension in said diaphragm during said movement; and
   immobilizing means situated on said body member and located within said first recess at about said central portion, said immobilizing means adapted to be contacted by at least one of said diaphragm and said suspension member and to substantially immobilize said diaphragm when said diaphragm is in said inner position so that said stethoscope head will pass low frequency sounds and attenuate high frequency sounds when said diaphragm is in said outer position and between said outer and inner positions, and when said diaphragm is in said inner position the acoustical stiffness of said diaphragm will be sufficiently higher than said first acoustical stiffness so that said head will pass high frequency sounds and attenuate low frequency sounds.

2. A stethoscope head in accordance with claim 1, further comprising a second conical-shaped recess located within said first bell-shaped recess and emanating from the base of said first bell-shaped recess, said second recess being formed by said immobilizing means and said central portion of said body member.

3. A stethoscope head in accordance with claim 1, wherein said suspension member is a cylindrical-shaped foam member.

4. A stethoscope head in accordance with claim 1, wherein said suspension member is a compression spring.

5. A stethoscope head comprising:
a body member having a first generally bell-shaped recess with an innermost central portion, an outer rim portion, and a bore extending through said body member communicating with said central portion of said first recess;
a diaphragm having a peripheral edge portion and a predetermined surface contour overlying at least a portion of said first recess and moveably connected to the outer rim portion of said first recess;
a compliant ring having an inner edge, an outer edge and a central curved portion, said inner edge being attached to said peripheral edge portion of said diaphragm and said outer edge being attached to said outer rim portion of said first recess to provide a first acoustical stiffness for said diaphragm, said compliant ring permitting movement of said diaphragm in a direction generally perpendicular to the plane of said diaphragm between a normal outer position to which said diaphragm is biased by said compliant ring and an inner position more closely adjacent said central portion of said first recess without substantially changing the surface contour of or the lateral tension in said diaphragm during said movement; and immobilizing means situated on said body member and located within said first recess at about the boundary between the outer rim portion and said inner central portion and together with said central portion forming second shallow and generally conical-shaped recess within said first recess, said immobilizing means adapted to be contacted by said diaphragm and to immobilize said diaphragm when said diaphragm is in said inner position so that said stethoscope head will pass low frequency sounds and attenuate high frequency sounds when said diaphragm is in said outer position and between said outer and inner positions, and when said diaphragm is in said inner position the acoustical stiffness of said diaphragm will be significantly higher than said first acoustical stiffness so that said stethoscope head will pass high frequency sounds and attenuate low frequency sounds.

6. A stethoscope head in accordance with claim 5, wherein said second conical-shaped recess is formed by a plate-like member having a gradually sloping central depression therein and a resilient O-ring circumjacent said plate-like member, said O-ring having a thickness which is greater in dimension than the maximum thickness of said plate-like member at its periphery and constituting said immobilizing means.

7. A stethoscope head in accordance with claim 6, wherein said diaphragm has a hole therein in order to facilitate movement of said diaphragm from its position adjacent said second recess when the stethoscope head is in use.

8. A stethoscope head in accordance with claim 5, wherein said suspension member has a curved portion therein.

9. A stethoscope head in accordance with claim 5, wherein said diaphragm comprises an epoxy resin-fiberglas blend and said suspension member comprises a material selected from the group consisting of elastomeric polyurethane and thermoplastic rubbers.

10. A stethoscope head in accordance with claim 5, wherein said diaphragm and said suspension member are formed as an integral member.

11. A stethoscope head in accordance with claim 2, wherein said central portion has a gradually sloping central depression therein and wherein a resilient o-ring which is circumjacent said central portion constitutes said immobilizing means, said o-ring having a thickness which is greater in dimension than the maximum thickness of said central portion at its periphery.

* * * * *